United States Patent
Lakowicz et al.

(10) Patent No.: US 6,660,379 B1
(45) Date of Patent: Dec. 9, 2003

(54) LUMINESCENCE SPECTRAL PROPERTIES OF CDS NANOPARTICLES

(75) Inventors: Joseph R. Lakowicz, Ellicott City, MD (US); Ignacy Gryczynski, Baltimore, MD (US); Zygmunt Gryczynski, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 09/890,042

(22) PCT Filed: Feb. 4, 2000

(86) PCT No.: PCT/US00/02954
§ 371 (c)(1),
(2), (4) Date: Jul. 25, 2001

(87) PCT Pub. No.: WO00/46839
PCT Pub. Date: Aug. 10, 2000

Related U.S. Application Data

(60) Provisional application No. 60/118,904, filed on Feb. 5, 1999.

(51) Int. Cl.[7] ................................. B32B 5/16
(52) U.S. Cl. ..................... 428/402; 428/403; 428/407; 313/502; 313/503; 252/500; 252/501.1; 252/518
(58) Field of Search ............... 428/402, 403, 428/407; 252/500, 501.1, 518; 313/502, 503

(56) References Cited

U.S. PATENT DOCUMENTS 5,938,934 A * 8/1999 Balogh et al. .............. 210/688
6,048,616 A * 4/2000 Gallagher et al. .......... 428/407

OTHER PUBLICATIONS

M. Brucher et al. "Semiconductor Nonocrystals as Fluorescent Biologicol Labels" Science vol. 281, Sep. 25, 1998.*
Bruchez, et al., "Semiconductor Nanocrystals as Fluroescent Biological Labels," Science, 281:2013–2016, 1998.

(List continued on next page.)

Primary Examiner—Leszek Kiliman
(74) Attorney, Agent, or Firm—David L. Marks

(57) ABSTRACT

The steady state and time resolved luminescence spectral properties of two types of novel CdS nanoparticles and nanoparticles are described. CdS nanoparticles formed in the presence of an amine-terminated dendrimer show blue emission. The emission wavelength of these nanoparticles depended on the excitation wavelength. The CdS/dendrimer nanoparticles display polarized emission with the anisotropy rising progressively from 340 to 420 nm excitation, reaching a maximal anisotropy value in excess of 0.3. A new constant positive polarized emission from luminescent nanoparticles is also described. Polyphosphate-stabilized CdS nanoparticles are described that display a longer wavelength red emission maximum than bulk CdS and display a zero anisotropy for all excitation wavelengths. Both nanoparticles display strongly heterogeneous intensity decays with mean decay times of 93 ns and 10 $\mu$s for the blue and red emitting particles, respectively. Both types of nanoparticles were several times more photostable upon continous illumination than fluorescein. In spite of the long decay times the nanoparticles are mostly insensitive to dissolved oxygen but are quenched by iodide. These nanoparticles can provide a new class of luminophores for use in chemical sensing, DNA sequencing, high throughput screening and other applications.

12 Claims, 12 Drawing Sheets

OTHER PUBLICATIONS

Mahtab, et al., "Preferential Adsorption of a "Kinked" DNA to a Neutral Curved Surface: Comparisons to and Implications for Nonspecific DNA—Protein Interactions," Journal of American Chemical Society, 118:7028–7032, 1996.

Mahtab, et al., "Temperature– and Salt–Dependent Binding of Long DNA to Protein–Sized Quantum Dots: Thermodynamics of "Inorganic Protein"—DNA Interactions," Journal of American Chemical Society, 122:14–17, 2000.

Mahtab, et al., "Protein–Sized Quantam Dot Luminescence Can Distinguish between "Straight", "Bent", and "Kinked" Oligonucleotides," Journal of American Chemical Society, 117:9099–9100, 1995.

Alivisatos, et al., "Organization of 'nanocrystal molecules' using DNA," Nature, 382:609–611, 1996.

Sooklal, et al., "Photophysical Properties of ZnS Nanoclusters with Spatially Localized Mn2+," The Journal of Physical Chemistry:100(10), 4551–4555, 1996.

Colvin, et al., "Light–emitting diodes made from cadmium selenide nanocrystals and a semiconducting polymer," Nature, 370:354–357, 1994.

Artemyev, et al., "Electroluminescence in thin solid films of closely–packed CdS nanocrystals," Journal of Crystal Growth, 184/185: 374–376, 1998.

Dabbousi, et al., "Electroluminescence from CdSe quantum–dot/polymer composites," Applied Phys. Lett., 66:1316–1318, 1995.

Zhang, et al., "Electrochemiluminescence from Calixarene–Coated Porous Si Liquid Junction Cells," Journal Phys. Chem. B, 101(35): 1997.

Artemyev, "Electroluminescence in thin solid films of closely packed CdS nanocrystals," J. Appl. Physics, 81(10): 6975–6977, 1997.

Hines, et al., "Bright UV–Blue Luninescent Colloidal ZnSe Nanocrystals," The Journal of Physical Chemistry B, 102(19): 3655–3656, 1998.

Brus, et al., "Electronic Spectroscopy and Photophysics of Si Nanocrystals: Relationship to Bulk c–Si and Porous Si," The Journal of American Chemical Soceity, 117(10): 2915–2922, 1995.

Huang, et al., "Photoluminescence and electroluminescence of ZnS:Cu nanocrystals in polymeric networks," Appl. Phys. Lett., 70(18): 2335–2337, 1997.

Bawendi, et al., "The Quantam Mechanics of Larger Semiconductor Clusters ("Quantum Dots")," Annu. Rev. Phys. Chem., 41:477–496, 1990.

Martin, et al., "Nanomaterials in Analytical Chemistry," Analytical Chemistry News & Features, 322 A–327 A, 1998.

Chan, "Quantum dot bioconjugates for ultrasenstive nonisotopic detection," Science, 281(5385):2016–8, 1998.

Correa–Duarte, "Stabilization of CdS semiconductor nanoparticles against photodegradation by a silica coating procedure," Chemical Physics Letters 286: 497–501, 1998.

Murphy, et al., "Quantum Dots as Inorganic DNA–Binding Proteins," Materials Research Society Symp.Proc., 452:597–600, 1997.

* cited by examiner

LUMINESCENCE SPECTRAL PROPERTIES OF CDS NANOPARTICLES

This patent application claims priority to U.S. patent application 60/118,904, filed on Feb. 5, 1999, and to International patent application PCT/US00/02954 filed on Feb. 4, 2000, copies of which are incorporated by reference.

The United States Government may have rights to this invention pursuant to the National Institute of Health (NIH), National Center for Research Resources, Grant No. RR-08119.

FIELD OF THE INVENTION

This invention relates to nanoparticle cadmium sulfide (CdS) fluorescent probes. Preferably, this invention relates to CdS nanoparticles formed in the presence of an amine-terminated dendrimer and/or polyphosphate-stabilized CdS particles both with average diameters or other critical dimensions (CDs) of several nanometers (nm).

BACKGROUND

There is presently widespread interest in the physical and optical properties of semiconductor particles with average diameters or CdS measured in nanometers. These particles are often called nanoparticles or quantum dots. The optical properties of such particles depends on their size [Martin, C. R.; Mitchell, D. T., Anal. Chem. (1998) 322A–327A].

Such particles display optical and physical properties which are intermediate between those of the bulk material and those of the isolated molecules. For example, the optical absorption of bulk CdSe typically extends to 690 nm. The longest absorption band shifts to 530 nm for CdSe nanoparticles with 4 nm average diameters [Bawendi, M. G.; et al., Annu. Rev. Phys. Chem. (1990) 41, 477–496].

Sizes of nanoparticies are usually measured by average diameters of equivalent spherical particles. For particles that are not at least approximately spherical, the smallest dimension (called critical dimension or CD) is often used. In nanoparticles a large percentage of the atoms are at the surface, rather than in the bulk phase. Consequently, the chemical and physical properties of the material, such as the melting point or phase transition temperature, are affected by the particle size. Semiconductor nanoparticles can be made from a wide variety of materials including, but not limited to CdS, ZnS, $Cd_3P_2$, PbS, $TiO_2$, ZnO, CdSe, silicon, porous silicon, oxidized silicon, and Ga/InN/GaN.

Semiconductor nanoparticles frequently display photoluminescence and sometimes electroluminescence. For example see Dabbousi, B. O., et al., Appl. Phys. Lett. (1995) 66(11), 1316–1318; Colvin, V. L., et al., Nature, (1994) 370, 354–357; Zhang, L., et al., J. Phys. Chem. B. (1997) 101 (35), 874–6878; Artemyev, M. V., et al, J. Appl. Phys., (1997) 81(10), 6975–6977; Huang, J., et al., Appl. Phys. Lett. (1997) 70(18), 2335–2337; and Artemyev, M. V., et al., J. Crys. Growth, (1988) 184/185, 374–376. Additionally, some nanoparticles can form self-assembled arrays.

Nanoparticles are being extensively studied for use in optoelectronic displays. Photophysical studies of nanoparticles have been hindered by the lack of reproducible preparations of homogeneous size. The particle size frequently changes with time following preparation. Particle surface is coated with another semiconductor or other chemical species to stabilize the particle [Correa-Duarte, M. A., et al., Chem. Phys. Letts. (1998) 286, 497–501; Hines, M. A., et al., J. Phys. Chem. (1996) 100, 468–471; and Sooklal, K., et al., J. Phys. Chem. (1996) 100, 4551–4555].

There are several examples of fluorescing cadmium sulfide nanoparticles. Tata, et al. use emulsions [Tata, M., et al., Colloids and Surfaces, 127, 39 (1997)]. Fluorescence of CdS nanocrystals have been observed by low temperature microscopy. Blanton, et al. show fluorescence from 5.5 nm diameter CdS nanocrystals with excitation of 800 nm and emission centered around 486 nm [Blanton, S., et al., Chem. Phys. Letts., 229, 317 (1994)]. Tittel, et al. noticed fluorescence of CdS nanocrystals by low temperature confocal microscopy [Tittel, J., et al., J. Phys. Chem. B, 101(16) (1997) 3013–3016].

A 64 branch poly(propylene imine) dendritic box can trap a Rose Bengal molecule (i.e., a polyhalogenated tetracyclic carboxylic acid dye) to allow it to strongly fluoresce since it is isolated from surrounding quenching molecules and solvents [Meijer, et al., Polym. Mater. Sci. Eng., (1995) 73, 123].

While the absorption and emission spectra of nanoparticles have been widely studied, the scope of these measurements were typically limited to using the optical spectra to determine the average size of the particles. There have been relatively few studies of the time-resolved photophysical properties of these particles.

The emission from silicon nanoparticles has been reported as unpolarized [Brus, L. E., et al., J. Am. Chem. Soc. (1995) 117, 2915–2922] or polarized [Andrianov, A. V., et al., JETP Lett. (1993) 58, 427–430; Kovalev, D., et al., Phys. Rev. Letts. (1997) 79(1), 119–122; and Koch, F., et al., J. Luminesc., (1996) 70, 320–332]. Polarized emission has also been reported for CdSe [Chamarro, M., et al., Jpn. J. Appl. Phys. (1995) 34, 12–14; and Bawendi, M. G., et al., J. Chem. Phys. (1992) 96(2), 946–954]. However, in these cases the polarization is either negative or becomes negative in a manner suggesting a process occurring within the nanoparticle. Such behavior would not be useful for a fluorescence probe for which the polarization is expected to depend on rotational diffusion.

The increasing availability of homogeneous sized nanoparticles suggests more detailed studies of their photophysical properties, which in turn could allow their use as biochemical probes. The first reports of such particles as cellular labels have just appeared [Bruchez, M., et al., Science (1998) 281, 2013–2016; and Chan, W., et al., Science (1998) 281, 2016–2018]. CdS particles have also been synthesized which bind DNA and display spectral changes upon DNA binding [Mahtab, R., et al., J. Am. Chem. Soc. (1996) 118, 7028–7032; and Murphy, C. J., et al., Proc. Materials Res. Soc. (1997) 452, 597–600].

U.S. Pat. No. 5,938,934 to Balogh et al., describes use of dendrimers as hosts for many materials including semiconductors. However the nanoparticles are somewhat large for use as a probe based on size. Only example 15 discloses cadmiums sulfide. However dangerous sulfide gas is used over prolonged periods of time.

SUMMARY

This invention describes fabrication methods, spectroscopy, probes and other applications for semiconductor nanoparticles. The preferred embodiments are two types of cadmium sulfide (CdS) nanoparticles. CdS nanoparticles formed in the presence of an amine-terminated dendrimer show blue emission. The emission wavelength of these nanoparticles depends on the excitation wavelength. These CdS/dendrimer nanoparticles display a new constant positive polarized blue emission. Polyphosphate-stabilized CdS nanoparticles are described that display a longer wavelength red emission maximum than bulk CdS and display a zero anisotropy for all excitation wavelengths. Both nanoparticles display strongly heterogeneous intensity decays with mean decay times of 93 ns and 10 μs for the blue and red emitting particles, respectively. Both types of nanoparticles were several times more photostable upon continuous illumination than fluorescein. In spite of the long decay times the nanoparticles are mostly insensitive to dissolved oxygen but are quenched by iodide. These nanoparticles can provide a new class of luminophores for use in chemical sensing, DNA sequencing, high throughput screening, fluorescence polarization immunoassays, time-gated immunoassays, time-resolved immunoassays, enzyme-linked immunosorbent assay (ELISA) assays, filtration testing, and targeted tagging and other applications.

DETAILED DESCRIPTION

Figure 1:
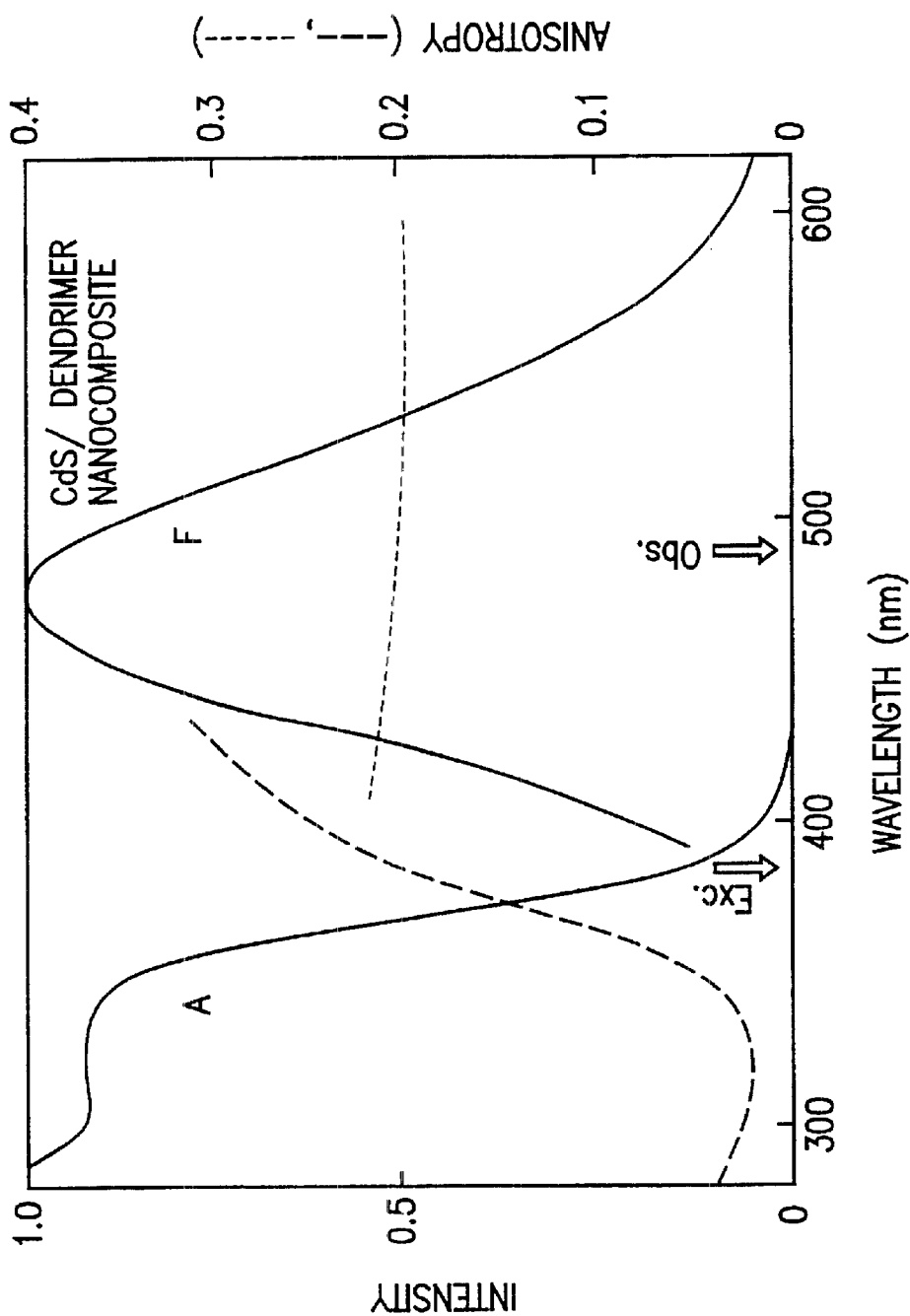
FIG. 1 shows absorption and emission spectra for the blue emitting CdS/dendrimer nanoparticle in methanol at room temperature. The excitation spectrum of this nanoparticles overlaps with the absorption spectrum. Also shown are the excitation and emission anisotropy spectra, also in methanol at room temperature.

This invention describes detailed studies of the steady state and time-resolved emission semiconductor nanoparticles. The preferred embodiments are two types of stabilized CdS particles. The first type of CdS nanoparticles were fabricated in the presence of a dendrimer and display blue emission. The second type of CdS particles were stabilized with polyphosphate and display red emission.

Semiconductor nanoparticles with fluoresce and/or luminesce more intensely and often at wavelengths shifted from their bulk counterparts. The nanoparticles of the present invention luminesce most strongly when they have average diameters and/or critical dimensions less than 5 nm. The nanoparticles of the present invention have a very narrow distribution of diameters and/or critical dimensions. In the preferred mode of this invention, at least 90% of a nanoparticle powder has critical dimensions of no more than +/−15% from the average diameter and/or critical dimension of the powder. This narrow particle size distribution is extremely important for maximizing emission intensity and other fluorescent properties.

The semiconductor nanoparticles of the present invention may be only one semiconductor, composites of several materials in each nanoparticle, and/or mixtures of different nanoparticles (e.g., powders, agglomerates, and/or aggregates). The individual nanoparticles can be uncoated, coated, partially coated, attached to a molecule, and/or trapped in a nanoscopic volumetric area. In one contemplated example, a semiconductor nanoparticle is coated with another semiconductor. The coating preferably has a higher bandgap than the core nanoparticle. In another contemplated example, electrically non-conductive coatings or anchor molecules control the size and spacing of the semiconductive nanoparticles. Coatings can also be used to protect the core nanoparticle from other effects such as, but not limited to, certain wavelengths, oxidation, quenching, size changes, size distribution broadening, and electronic conductivity. There may be more than one coating layer and/or material.

The nanoparticles of the present invention have at several important improvements. First, the dendrimer-based and other types of template-based nanoparticles show polarized emission. Polarization offers many advantages and an additional variable over prior fluorescent nanoparticle spectroscopy. Second, the nanoparticles of the present invention are very resistant to quenching by oxygen or other dissolved species. This important advance avoids the quenching problems that plague much of fluorescence spectroscopy. Third, the nanoparticles of the present invention have long wavelength emission. Emission wavelengths of above 500 nm possible with the present invention are especially suitable for biological sensing and minimize autofluorescent noise. Fourth, the nanoparticles of the present invention have long lifetimes. Lifetimes of 30 ns to well over 100 ns are possible with this invention even in the presence of fluorescence quenchers. Long lifetimes allow use of smaller and less expensive spectrometers, sensors and detectors. The combination of long lifetimes with long fluorescence decay times are particularly valuable.

This invention's preferred mode describes solution phase nanofabrication of semiconductor nanoparticles. Solution phase nanofabrication is much less expensive than most types of nanofabrication using vacuum systems, electrochemistry, special ball mills, electric arcs, gas phase chemistry, etc. This invention's nanoparticles can be made in bulk or within a template such as, but not limited to, a dendrimer membrane or dendrimer-modified optical fiber. This invention avoids the use of dangerous and expensive reactive gases such as sulfide gas.

CdS/Dendrimer Nanoparticle

FIG. 1 shows the absorption and emission spectra of the CdS/dendrimer particles. There is a substantial Stokes' shift from 330 to 480 nm. Such a large Stokes' shift is a favorable property because the emission of the nanoparticles will be observable without homo-energy transfer between the particles. Also, because of the substantial shift it should be relatively easy to eliminate scattered light from the detected signal by optical filtering. The term nanoparticle in this invention is meant to include nanocomposites, clusters of nanoparticles, agglomerates of generally electrically isolated nanoparticles and surface-modified nanoparticles as well as single material particles.

The emission intensity of the blue nanoparticles is relatively strong. The relative quantum yield is estimated by comparing the fluorescence intensity with that of a fluorophore of known quantum yield, and an equivalent optical density at the excitation wavelength of 350 nm. A solution of coumarin 1 in ethanol with a reported quantum yield of 0.73 was used as a quantum yield standard. This comparison yields an apparent or a relative quantum yield of 0.097. This value is not a molecular quantum yield because there is no consideration of the molar concentration of the nanoparticles. However, this value does indicate the relative brightness of the particles as compared to a known fluorophore. This value is somewhat lower than the previously reported quantum yield of approximately 0.17 [Murphy, C. J., Brauns, E. B., and Gearheart, L. (1997), Quantum dots as inorganic DNA-binding proteins, *Proc. Materials Res. Soc.* 452, 597–600]. It is possible that the quantum yields differ for different preparations of the nanoparticles.

Figure 2:
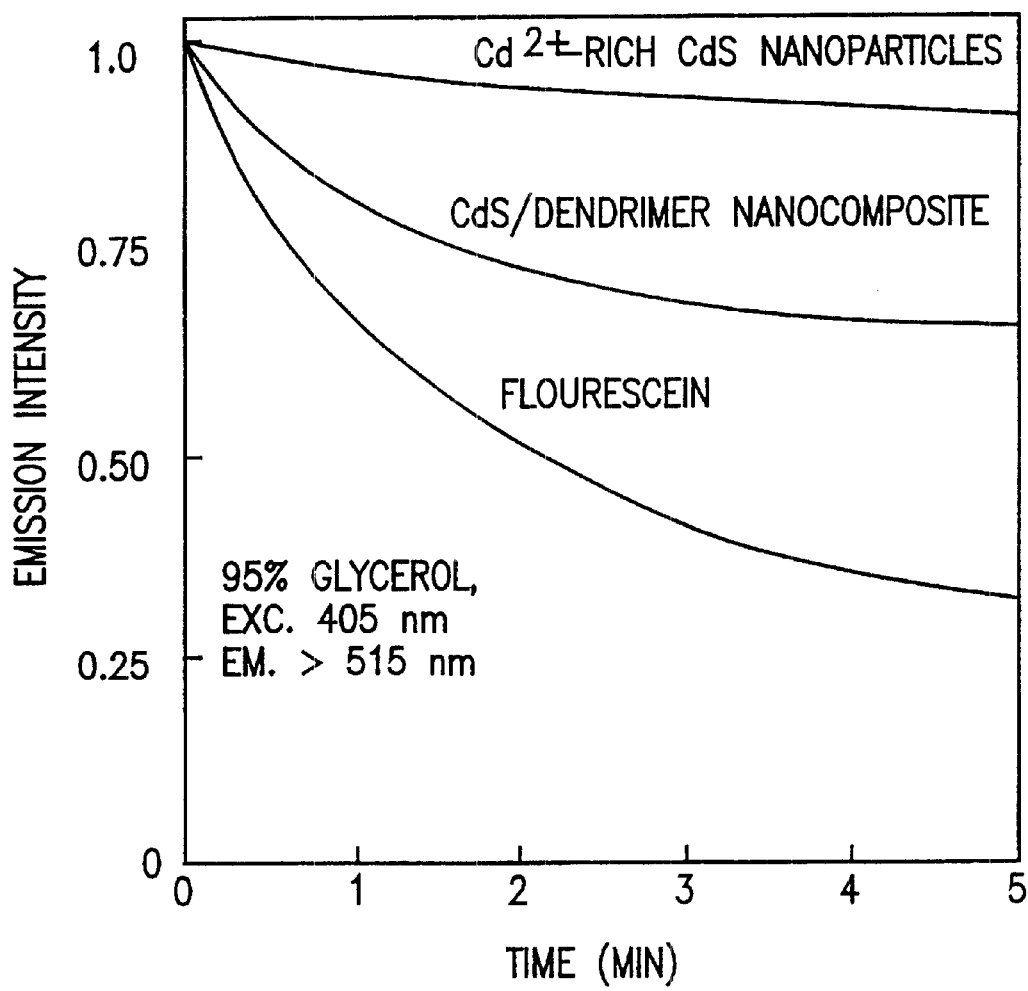
FIG. 2 shows photostability tests of the CdS/dendrimer and polyphosphate-stabilized (PPS) nanoparticles. The sample was contained in a standard 1 cm×cm (4 mL) cuvette. The incident power was 30 mW at 405 nm from a frequency-doubled Ti:Sapphire laser, 80 MHz, 200 fs, which was focused with a 2 cm focal length lens. Also shown is the intensity from fluorescein, pH 8, under comparable conditions. When illuminated with the output of a 450 W xenon lamp (385 nm for blue and 405 nm for red nanoparticles) there was no observable photobleaching.

For use as a luminescent probe the signal from the nanoparticles must be stable with continual illumination. The emission intensities and/or emission spectra of nanoparticles occasionally depend on illumination. In contrast, the CdS/dendrimer particles appear to be reasonably stable and about two-fold more stable than fluorescein (FIG. 2). In these stability tests the fluorescein and nanoparticles were illuminated with the focused output of a frequency-doubled Ti:Sapphire laser. No changes in the emission intensity of the nanoparticles were found when illuminated with the output of a 450W xenon lamp and monochromator.

For use as a biophysical probe of hydrodynamics a luminophore must display polarized emission. Since most nanoparticles are thought to be spherical, the emission is not expected to display any useful polarization. Importantly, the CdS/dendrimer nanoparticles of the present invention display high anisotropy (FIG. 1). This anisotropy increases progressively as the excitation wavelength increases across the long wavelengths side of the emission, from 350 to 430 nm. The emission anisotropy is relatively constant across the emission spectra. These properties, and the fact that the anisotropy does not exceed the usual limit of 0.4, suggest that the emission is due to a transition dipole similar to that found in excited organic molecules. The high and non-zero anisotropy also suggests that the excited state dipole is oriented within a fixed direction within the nanoparticles.

Figure 4:
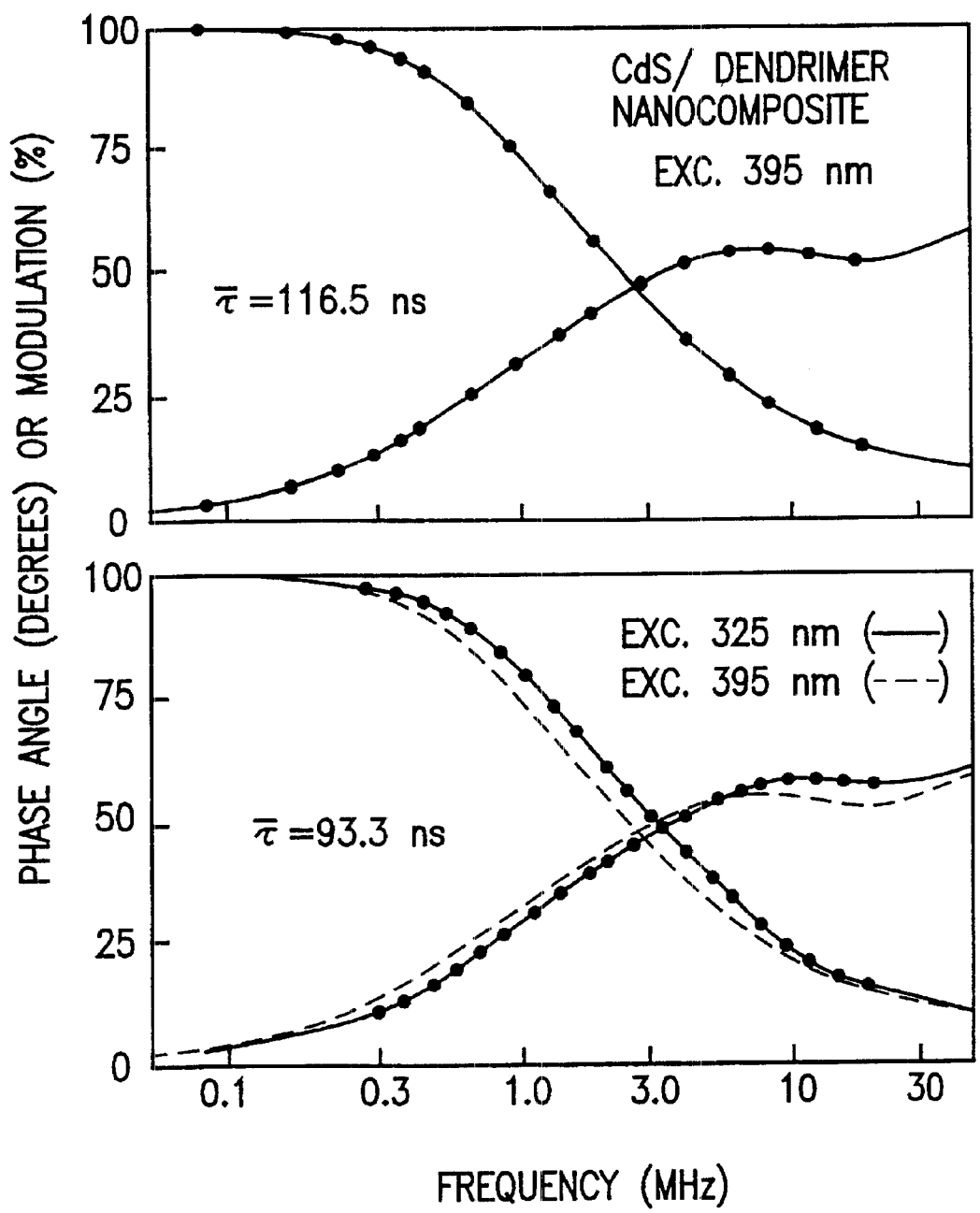
FIG. 4 shows a frequency-domain intensity decay of the CdS/dendrimer nanoparticle for excitation at 395 nm (top) and 325 nm (bottom). This solid line shows the best three decay time fit to the data.

A fixed direction for the electronic transition suggests the presence of some molecular features which define a preferred direction for the transition moment. While most nanoparticles are thought to be spherical, the shape of the CdS inside of the CdS/dendrimer nanoparticle is not known. Electron micrographs show that the particles and dendrimers exist as larger aggregates rather than as isolated species. Unfortunately, the presence of aggregates prevented determination of the particle shape. Our observation of a large non-zero anisotropy for these particles suggests an elongated shape for the quantum-confined state. This is the first constant positive polarized emission from CdS nanoparticles. The results in FIG. 2 suggest that CdS/dendrimer nanoparticles can serve as hydrodynamic probes for rotational motions on the 50 to 400 ns timescale (see FIG. 4 below).

Figure 3:
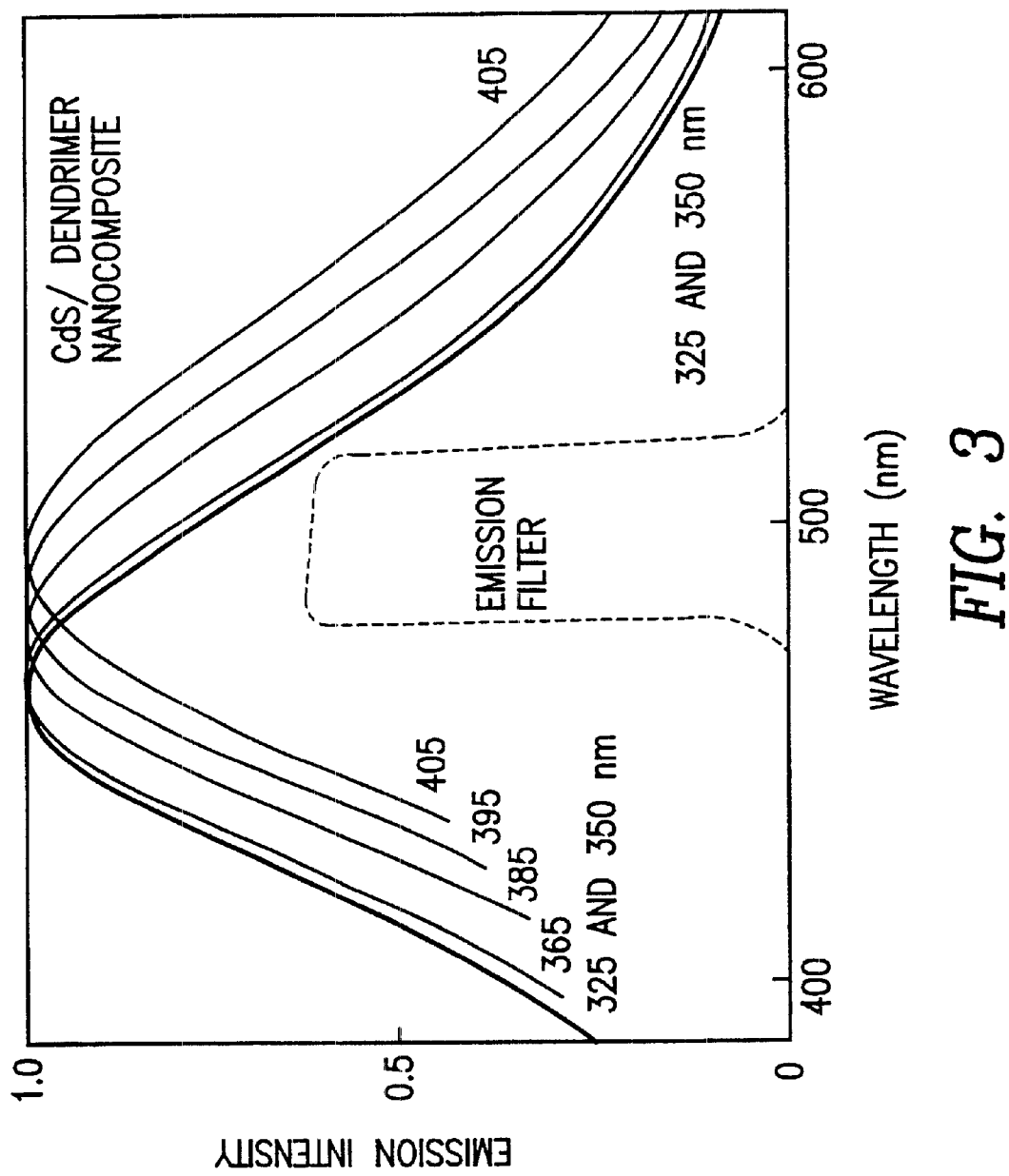
FIG. 3 shows emission spectra of the CdS/dendrimer composite for different excitation wavelengths. Also shown as the dashed line is the transmission profile of the filter used for the time-resolved measurements.

If the particle preparation has a single particle size, the emission spectra are expected to be independent of excitation wavelength. Hence we recorded the emission spectra for the CdS/dendrimer particles for a range of excitation wavelengths (FIG. 3). Longer excitation wavelengths results in a progressive shift of the emission spectra to longer wavelengths. This effect is reminiscent of the well-known red edge excitation shift observed for organic fluorophores in polar solvents. However, the molecular origin of the shift seen in FIG. 3 is different. In this case the shifts are probably due to the wavelength-dependent excitation of a selected sub-population of the particles at each wavelength. In particular, longer excitation wavelengths probably results in excitation of larger particles with a longer wavelength emission maximum. Hence this particular preparation of CdS/dendrimer particles appears to contain a range of particle sizes. However, we cannot presently exclude other explanations for the wavelength-dependent spectra seen in FIG. 3.

We examined the time-resolved intensity decay of the CdS/dendrimer particles using the frequency-domain (FD) method [J. R. Lakowicz and I. Gryczynski, Topic in Fluorescence Spectroscopy, Vol I, Techniques, Plenum Press, New York, pp 293–355]. The frequency responses were found to be complex (FIG. 4), indicating a number of widely spaced decay times. The FD data could not be fit to a single or double decay time model (Table I). Three decay times were needed for a reasonable fit to the data, with decay times ranging from 3.1 to 170 ns. The mean decay time is near 117 ns. There seems to be a modest effect of excitation wavelength. The mean decay time decreases from 117 ns for excitation at 395 nm to 93 ns for excitation at 325 nm. Such long decay times are a valuable property for a luminescent probe, particularly one which can be used as an anisotropy probe. The long decay time allows the anisotropy to be sensitive to motions on a timescale comparable to the mean lifetime. Hence, it is envisioned to use these nanoparticles as probes for the dynamics of large macro molecular structures, or even as model proteins since the nanoparticle size is comparable to the diameter of many proteins.

Figure 5:
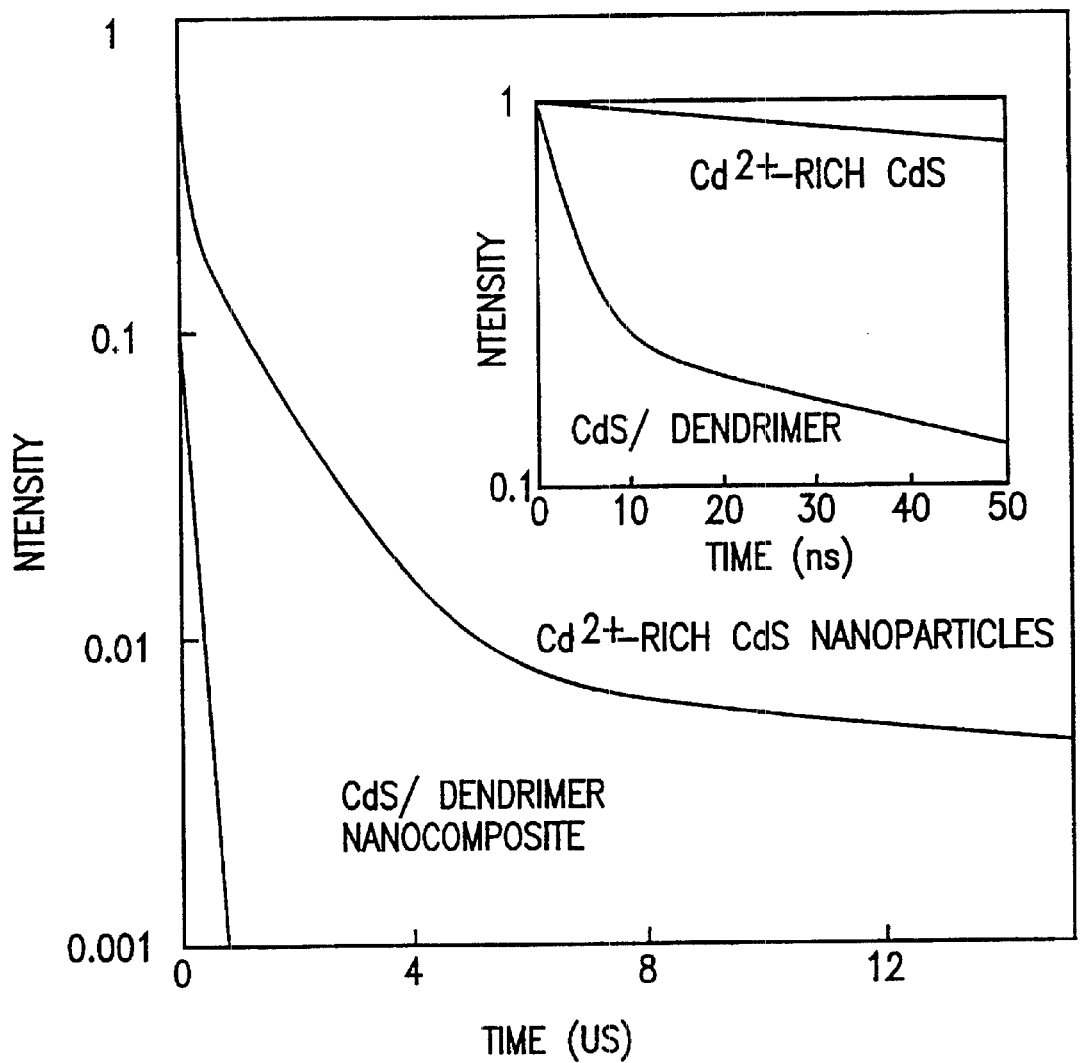
FIG. 5 shows time-dependent intensity decays of the nanoparticles reconstructed from the frequency-domain data (Tables I and II).

To better visualize the intensity decays, the parameters ($\alpha_i$ and $\tau_i$) recovered from the least-squares analysis in Table I were used to reconstruct the time-dependent intensity decays (FIG. 5). The intensity is multi- or non-exponential at early times (insert), but does not display any long-lived microsecond components. While the intensity decay could be fit to three decay times, it is possible that the actual decay is more complex, and might be more accurately represented as a distribution of decay times.

Figure 6:
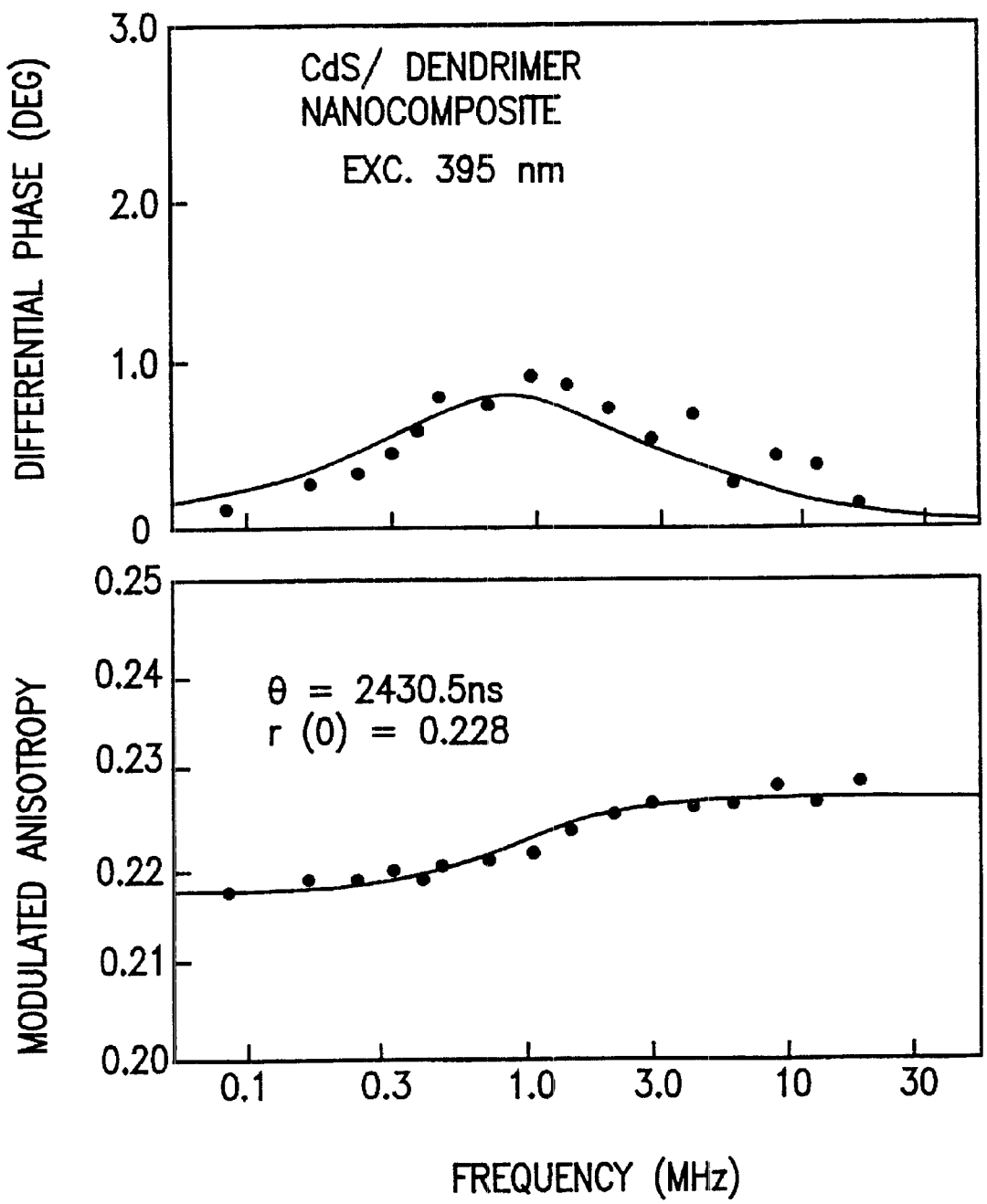
FIG. 6 shows a frequency-domain anisotropy decay of the CdS/dendrimer nanoparticle for excitation at 395 nm, at room temperature in methanol.

In the frequency-domain anisotropy decay of the CdS/dendrimer particles (FIG. 6), the differential polarized phase angles are rather low, with the largest phase angles centered near 1.0 MHz, suggesting rather long correlation times for the particles. Least squares analysis of the FD anisotropy data revealed a correlation time near 2.4 µs (Table I). Such a long correlation time is consistent with the observation that the CdS nanoparticles are aggregated with the dendrimers, or somehow present in a composite structure. Much shorter correlation times would be expected for particles with sizes near 2 nm that would be consistent with the optical properties. The time-zero anisotropy recovered from the FD anisotropy data is consistent with that expected from the excitation anisotropy spectra and the excitation wavelength. This agreement suggests that the anisotropy of these particles decays due to overall rotational motion, and not due to internal electronic properties of the particles. It is envisioned that these nanoparticles (especially when not aggregated) are useful as analogues of proteins or other macromolecules, and as internal cellular markers which could report the rate of rotational diffusion.

Dendrimers are macromolecules such as poly(amidoamine-organosilicon) containing hydrophilic and hydrophobic nanoscopic domains. The dendrimer have a dense star architecture which is a macromolecular structure with chains that branch from a central initiator core. Dendrimers have narrow molecular weight distributions with specific sizes and shapes. The dendrimers grow larger with each generation. For example, a generation 4 dendrimer is smaller than a generation 5 dendrimer. Dendrimers also have highly functional and accessible terminal surfaces. In the preferred embodiment of this invention, this terminal surface has amine which can bind cadmium. In the present invention, each dendrimer preferably holds a plurality of cadmium sulfide or other semiconductor nanoparticles. Creating semiconductor nanoparticles in dendrimer-based nanoscopic molecular sponges and dendrimer-based network materials (e.g., elastomers, plastomer, coatings, films and membranes) are also envisioned. The present invention can any non-conductive system having nanoscopic domains capable of binding a semiconductor. Envisioned examples include, but are not limited to, dendrimers, star polymers, self-assembling polymers, and zeolites.

Polyphosphate-Stabilized CdS Nanoparticles

Figure 7:
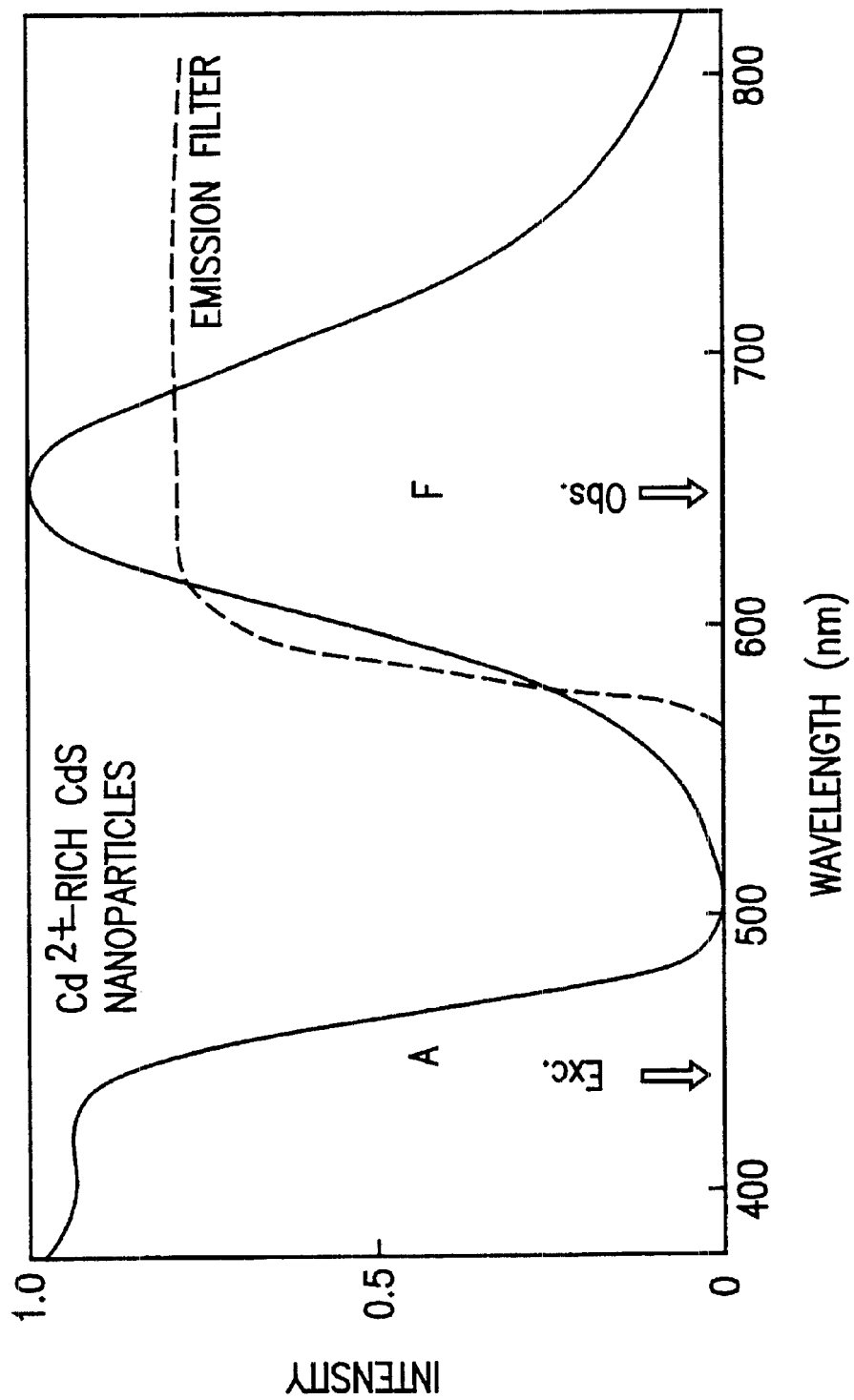
FIG. 7 shows absorption (A) and emission (F) spectra of the CdS/PPS nanoparticles. In this case the emission spectra were found to be independent of excitation wavelengths from 325 to 450 nm. The dashed line shows the transmission of the filter used to record the time-resolved data.

Other CdS nanoparticles in this invention, called CdS/PPS, have surfaces stabilized with polyphosphate (PPS). Absorption and emission spectra of these particles are shown in FIG. 7. Compared to the CdS/dendrimer nanoparticles, these stabilized nanoparticles absorbs and emit at much longer wavelengths. Their average diameter was estimated to be 4 nm±15% by transmission electron microscopy. The spectra and intensities were found to be stable with prolonged illumination and at least four-fold more stable than fluorescein (FIG. 2). The emission intensity of these red-emitting particles is considerably weaker than the blue particles. The apparent quantum yield of the red particles was measured relative to 4-(dicyanomethylene)-2-methyl-6-(4-dimethylamino-styryl)-4H-pyran (DCM) in methanol, with an assumed quantum yield of 0.38. For equivalent optical densities at the excited wavelength of 442 nm, these particles display an apparent quantum yield of 0.015, and are thus less bright than the blue-emitting CdS/dendrimer nanoparticles.

Compared to the blue-emitting nanoparticles, these red emitting particles display simpler properties. The emission spectra are independent of excitation wavelength, suggesting a narrow size distribution. The excitation spectrum (not shown) overlapped with the absorption spectrum. These nanoparticles can be made to have a long wavelength absorption above 480 nm. The absorption and excitation spectra of the CdS/dendrimer particles also appeared to be identical (FIG. 1).

Excitation and emission anisotropy spectra of these polyphosphate-stabilized nanoparticles show zero anisotropy for all excitation and emission wavelengths. The zero anisotropy values could be due to rotational diffusion of the particles during these long luminescence decay (below).

Figure 8:
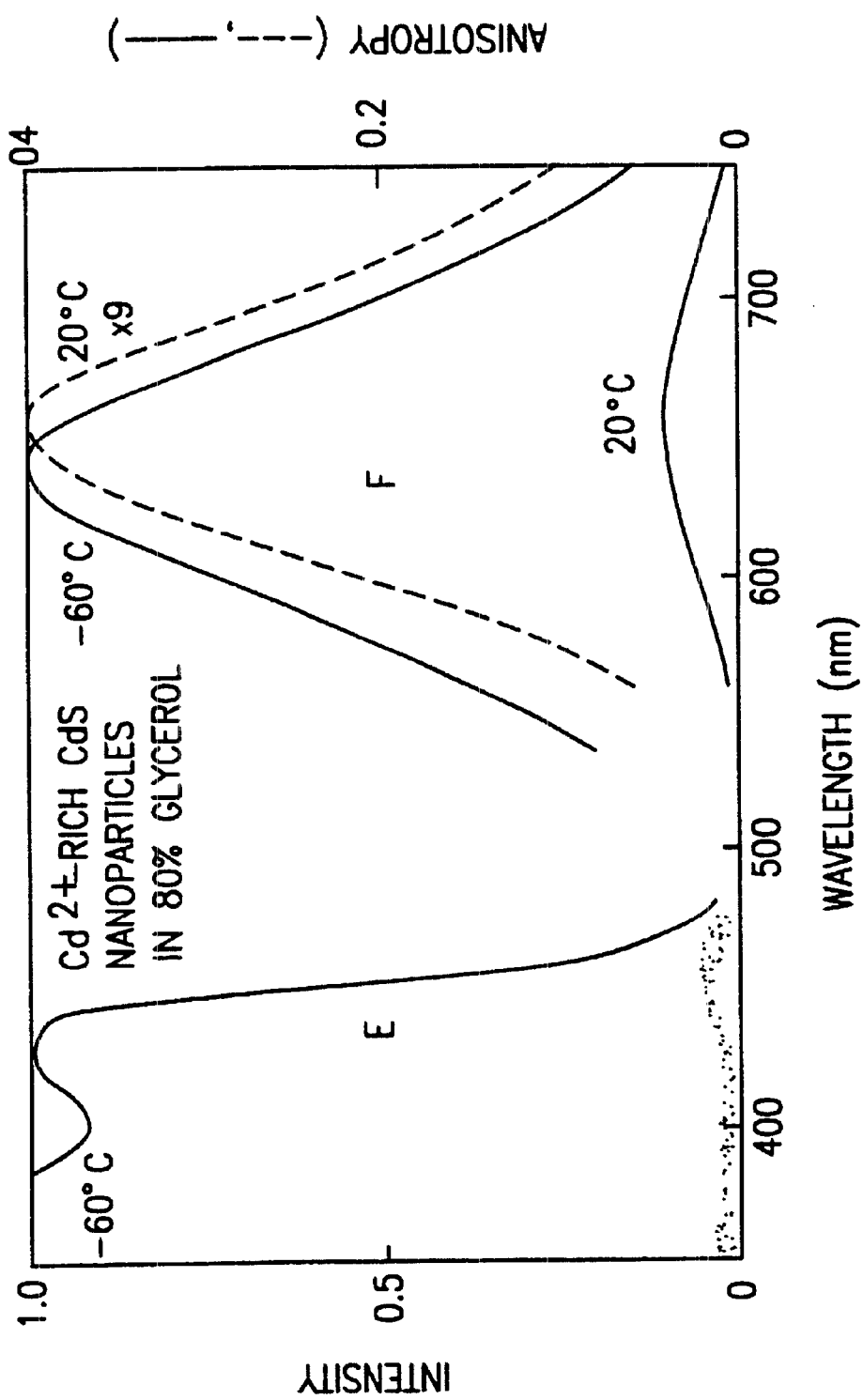
FIG. 8 shows excitation anisotropy spectra of the CdS/PPS nanoparticles in 80% glycerol at −60° C. (dots). Also shown are the temperature dependent spectra in 80% glycerol.

However, time-dependent decay of the anisotropy is not detected, as seen from the frequency-domain anisotropy data. The nanoparticles in 80% glycerol at −60° C. also show the anisotropies to be zero for excitation from 350 to 475 nm (FIG. 8). These results suggest that polarized emission is not a general property of nanoparticles, but requires special conditions of synthesis or stabilizers.

Figure 9:
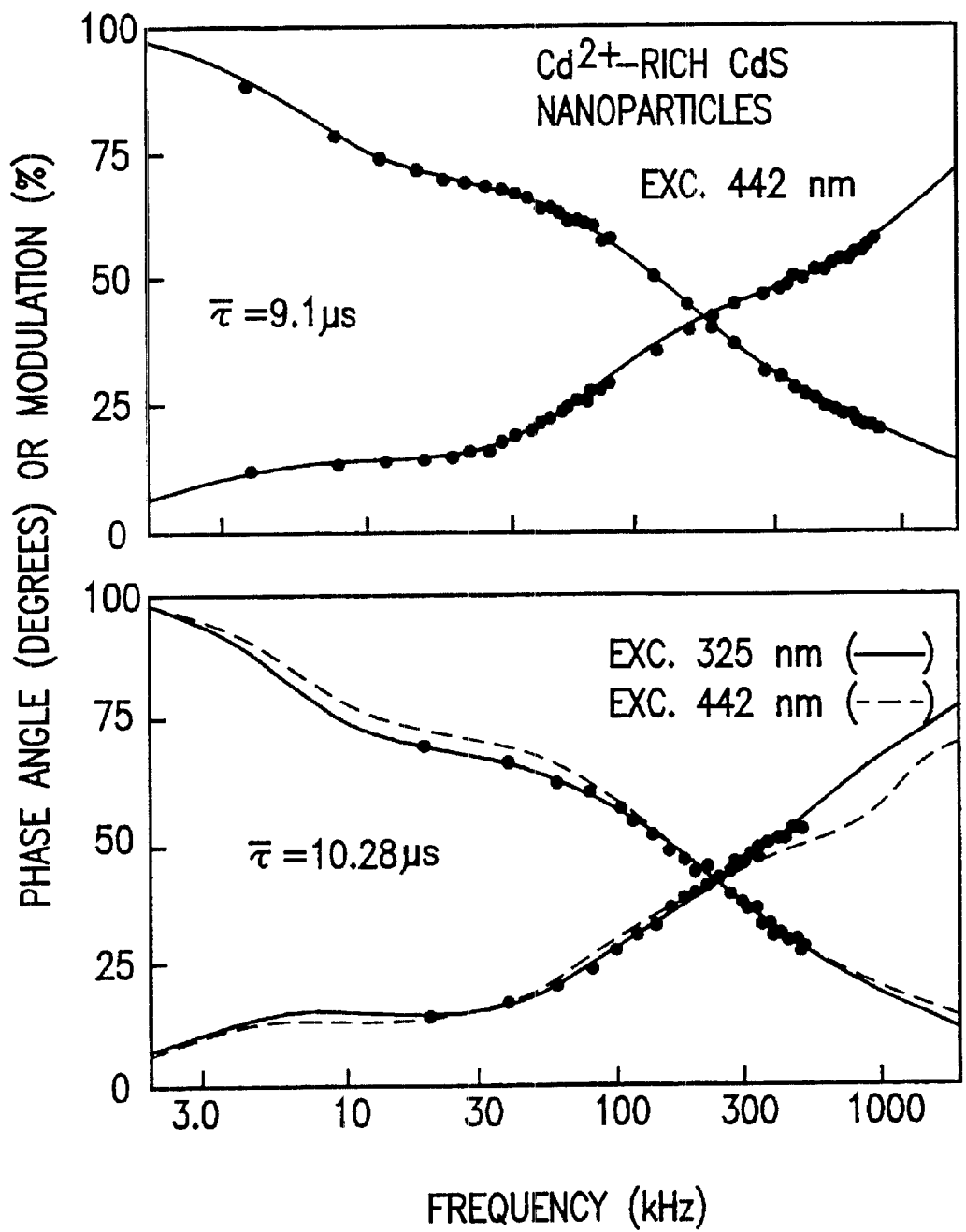
FIG. 9 shows a frequency-domain intensity decay of the CdS/PPS nanoparticles for excitation at 442 nm (top) and 325 nm (bottom). The solid lines show the best three decay time fits to the data.

The frequency-domain intensity decay of the PPS-stabilized nanoparticles is shown in FIG. 9. The intensity decay is complex, again requiring at least three decay times to fit the data (Table Ii). The intensity decay in the time domain is shown in FIG. 5. The decay times range from 150 ns to 25.3 µs, with a mean decay time near 9 µs. Once again there was an effect of excitation wavelength, but less than seen with the blue-emitting CdS/dendrimer nanoparticles.

Observation of microsecond decay times for these red emitting particles is an important result. There is currently considerable interest in using red or near infrared (NIR) probes for non-invasive and/or in-vivo measurements. Most such probes display relatively short decay times, typically less than 1 ns. While a few metal-ligand complexes are known to emit in the red and to display long lifetimes the choice of probes with long lifetimes are limited. These intensity decay data for the polyphosphate-stabilized nanoparticles suggest that such nanoparticle probes can provide a new class of luminophores with both long wavelength emission and long decay times.

Figure 10:
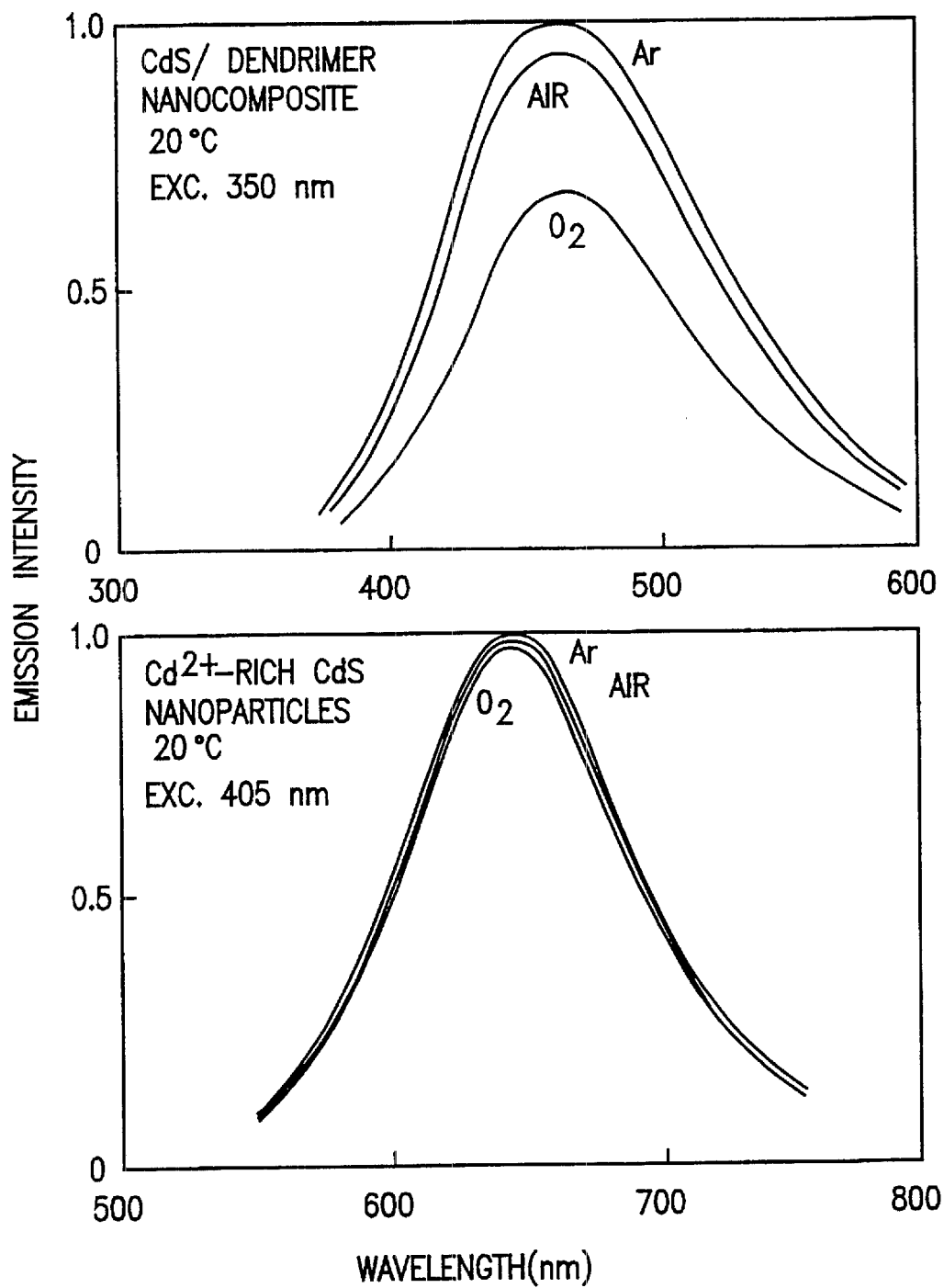
FIG. 10 shows the effect of oxygen on the emission spectra of the CdS/dendrimer and CdS/PPS nanoparticles.
Figure 11:
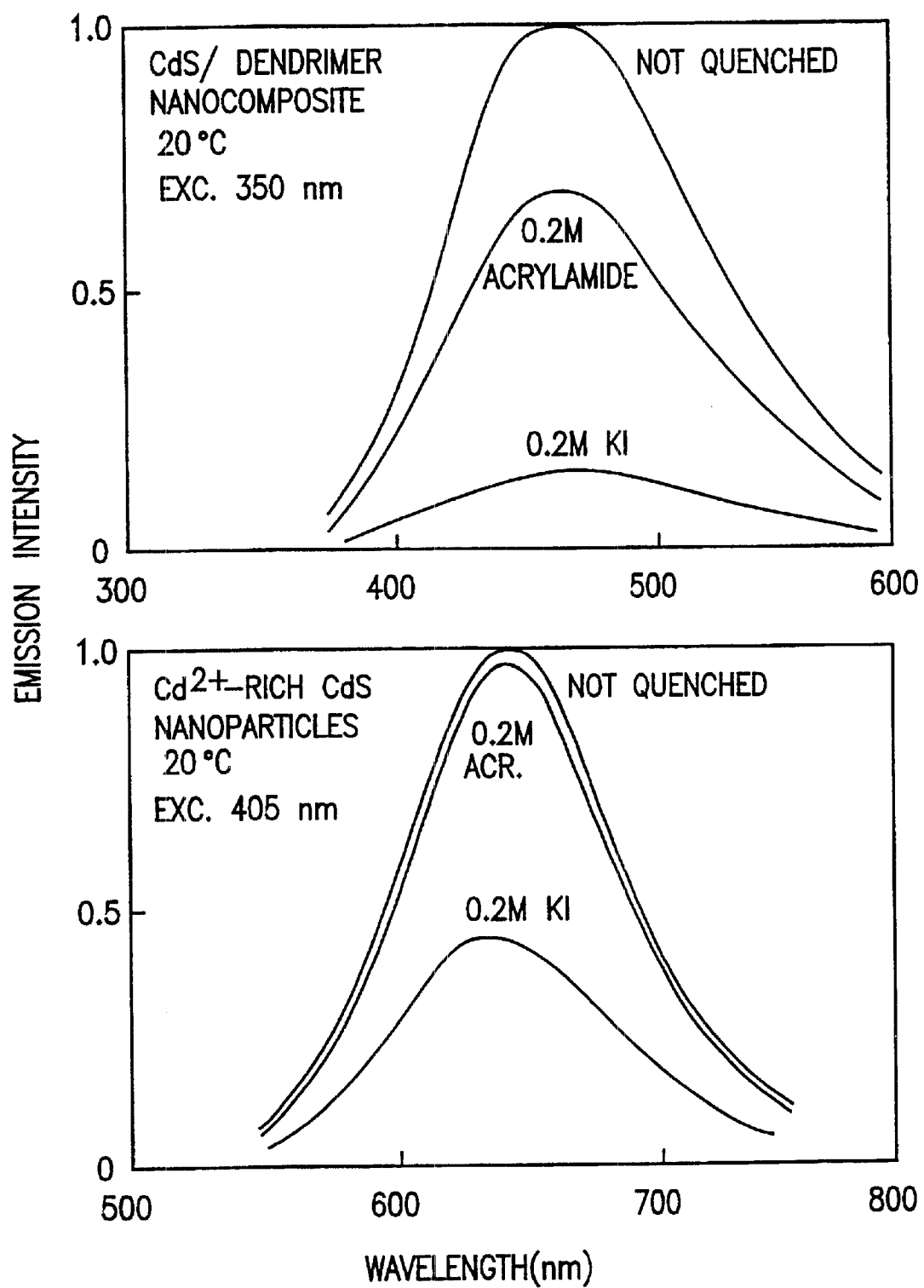
FIG. 11 shows the effect of acrylamide and iodide on the emission spectra of the CdS/dendrimer and CdS/PPS nanoparticles.
Figure 12:
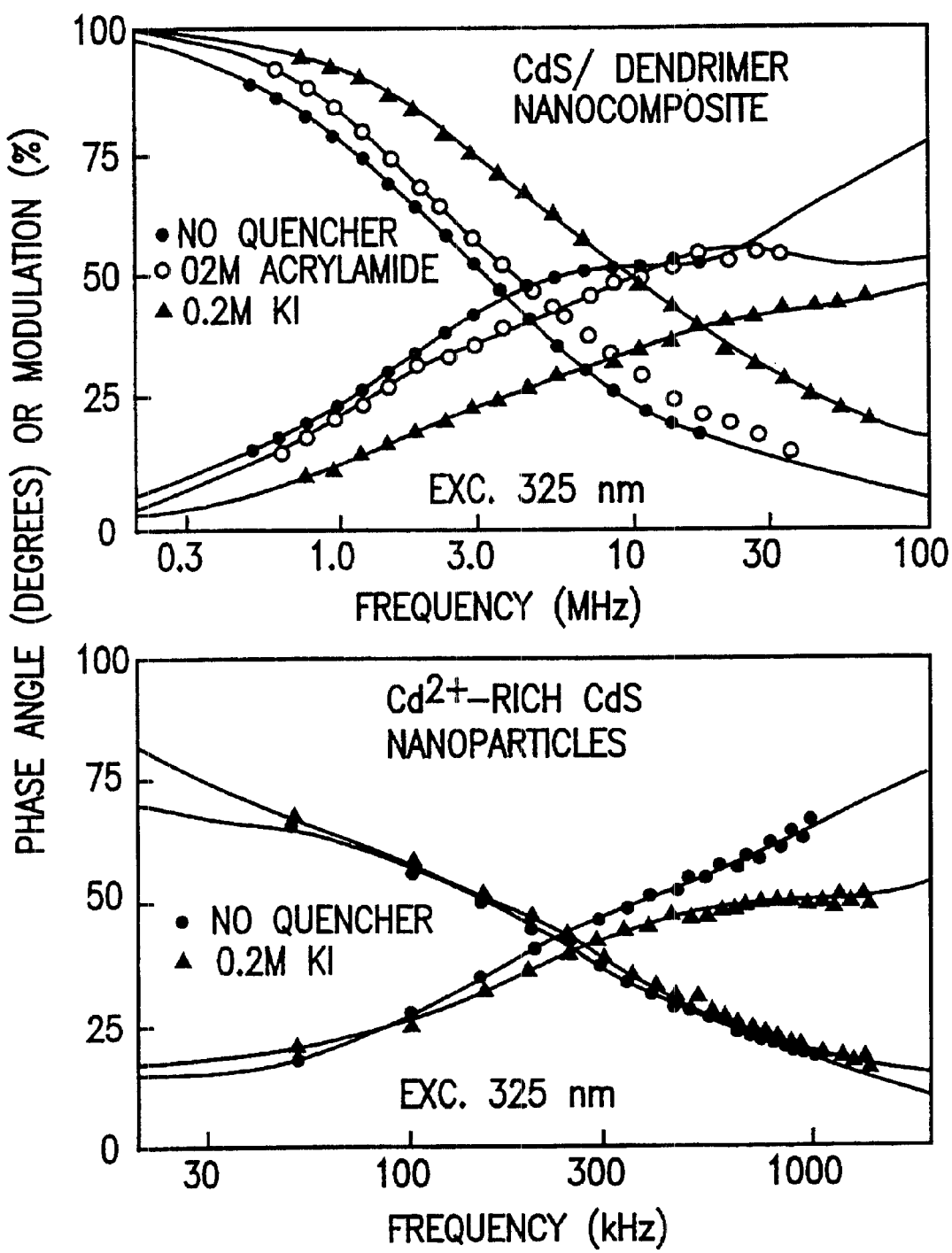
FIG. 12 shows intensity decays of the CdS/dendrimer (top) and CdS/PPS nanoparticles (bottom) in the absence and presence of 0.2 M acrylamide or 0.2 M iodide. These measurements were done independently of those presented in FIGS. 4 and 9. For the CdS/dendrimer nanoparticle (top panel) the recovered average lifetimes ($\tau = \Sigma f_i \tau_i$) are: 106.0 ns for not quenched (●), 73.7 ns in presence of 0.2 M acrylamide (○) and 36.7 ns in presence of 0.2 M KI (▼). For the CdS/PPS nanoparticles (lower panel) average lifetimes are 9.80 μs for not quenched (●), 8.45 μs in presence of 0.2 M acrylamide (not shown), and 4.09 μs in presence 0.2 M KI (▼).

Commonly used quenchers sometimes do not affect nanoparticle emission. The effect of oxygen are shown in FIG. 10. Dissolved oxygen had a modest effect on the intensity from the CdS/dendrimer particles, with the emission being quenched by about 40% for equilibration at one atmosphere of oxygen (top). Remarkably, dissolved oxygen had no effect on the emission from the CdS/PPS particles (lower panel). This is particularly surprising given the long intensity decay time of these particles. The absence of quenching by oxygen could be a valuable result. For instance, the absence of oxygen quenching is a valuable property of the lanthanides, allowing long decay times in samples exposed to air. These results suggest that some nanoparticles may be insensitive to oxygen, and thus useful for high sensitivity gated detection as is used in the lanthanide-based immunoassays. The CdS/dendrimer nanoparticles were quenched by both iodide and acrylamide (FIG. 11, top). The CdS/PPS particles were quenched by iodide but not significantly by acrylamide (bottom). The quenching observed for both types of nanoparticles seems to be at least partially dynamic, as seen by the decrease in mean decay time (Table III).

Many potential applications of nanoparticles as luminescent probes are envisioned. Red-NIR emitting probes with long decay times and optionally resistance to oxygen quenching are envisioned. A favorable property of the nanoparticles is the long intensity decay times. This allows those particles which display anisotropy to be used in hydrodynamic probes on the timescales ranging from hundreds of nanoseconds to microseconds. This is a timescale not usually available to fluorescence without the use of specialized luminophores. The luminescence decay times can be adjusted by changes in nanoparticles and nanoparticle composition, morphology, size, shape and surface modifications.

It is envisioned that the nanoparticles of the present invention could display resonance energy transfer. For example, the nanoparticles could display resonance energy transfer to absorbing dyes or could display Förster transfer.

Sensors incorporating the nanoparticles of the present invention are also envisioned for chemical, biological, optical and other applications. Preferred embodiments are sensors for important species such as $Ca^{2+}$, pH and/or chloride. Attachment of analyte-dependent absorbers to the nanoparticles are envisioned for analyte-dependent emission.

Preferred methods of making the nanoparticles of the present invention are described in Examples 1–2. Preferred methods of spectroscopic measurements of the nanoparticles of the present invention are described in Example 3.

EXAMPLE 1

Nanofabrication of CdS/dendrimer Nanoparticles

The blue emitting CdS particles were prepared in the presence of poly(aminoamine) STARBURST® dendrimer, generation 4.0 (bow Corning, Midland, Mich.; Dendritech™, Inc., Midland, Mich.; Michigan Molecular Institute, Midland, Mich.; Aldrich, Allentown, Pa.). The STARBURST® dendrimer (PAMAM) of generation 4.0 was purchased from Aldrich. This dendrimer is expected to have 64 surface amino groups. Based on the manufacturer's value of the dendrimer weight fractions in methanol, and the known dendrimer densities, we prepared dendrimer stock solutions of $1.14 \times 10^{-4}$ M in methanol under a $N_2$ atmosphere at 10° C. The 2.0 mM stock solutions of $Cd^{2+}$ and $S^{2-}$ were prepared by dissolving 62 mg of $Cd(NO_3)_2 \cdot 4H_2O$ (Baker) in 100 mL of methanol, and by dissolving 15 mg $Na_2S$ (Alfa) in 100 mL of methanol. The $Cd^{2+}$ and $S^{2-}$ stock solutions were freshly prepared. In the standard incremental addition procedure, an 0.50 mL aliquot of $Cd^{2+}$ stock solution was added to 10 mL of the dendrimer stock solution at 10° C., followed by addition of an 0.50 mL aliquot of $S^{2-}$ stock solution. The $Cd^{2+}$ and $S^{2-}$ additions were repeated 10 times. The resulting solution was colorless and glowed bright blue under UV Illumination. The product was stored in a freezer and did not show any evidence of precipitation for months. This nanoparticle dendrimer composite was stable for long periods of time in neutral methanol.

EXAMPLE 2

Nanofabrication of CdS/PPS Nanoparticles

The red emitting particles are also composed of CdS, but stabilized with polyphosphate [Mahtab, R., Rogers, J. P., and Murphy, C. J. (1995), Protein-sized quantum dot luminescence can distinguish between "straight", "bent," and "kinked" oligonucleotides, *J. Am. Chem. Soc.* 117, 9099–9100]. For the polyphosphate-stabilized (PPS) CdS/PPS nanoparticles, $2 \times 10^{-4}$ M $Cd(NO_3)_2 \cdot 4H_2O$ in degassed water was mixed with an equivalent amount of sodium polyphosphate, $Na_6(PO_3)_6$. Solid $Na_2S$ was added, with vigorous stirring, to yield $2 \times 10^{-4}$ M sulfide. The solution immediately turned yellow. Under UV light, the solution glowed red-orange.

EXAMPLE 3

Spectroscopic Measurements

Frequency-domain (FD) intensity and anisotropy decays were measured with a fluorescence spectrometer and standard fluorescence techniques [J. R. Lakowicz and I. Gryczynski, Topic in Fluorescence Spectroscopy, Vol I, Techniques, Plenum Press, New York, pp 293–355]. The excitation source was a HeCd laser with an emission wavelength of 325 nm or 442 nm. The continuous output of this laser was amplitude modulated with a Pockels' cell. The FD data were interpreted in terms of the multi-exponential model:

$$I(t) = \sum_i \alpha_i \exp(-t/\tau_i) \quad (1)$$

where $\alpha_i$ are the pre-exponential factors and $\tau_i$ are the decay times. The fractional contribution of each decay time component to the steady state emission is given by $$f_i = (\alpha_i \tau_i) / \left( \sum_j \alpha_j \tau_j \right) \quad (2)$$

Frequency-domain anisotropy decay data were measured and analyzed as described previously [Lakowicz, J. R., Cherek, H., Kusba, J., Gryczynski, I., and Johnson, M. L. (1993), Review of fluorescence anisotropy decay analysis by frequency-domain fluorescence spectroscopy, *J. Fluoresc.* 3, 103–116] in terms of multiple correlation times:

$$r(t) = \sum_k r_{0k} \exp(-t/\theta_k) \quad (3)$$

In this expression $r_{0k}$ is the fractional anisotropy amplitude which decays with a correlation time $\theta_k$.

The foregoing examples are illustrative embodiments of the invention and are merely exemplary. A person skilled in the art may make variations and modification without departing from the spirit and scope of the invention. All such modifications and variations are intended to be included within the scope of the invention as described in this specification and the appended claims.

TABLE I

Frequency-domain intensity and anisotropy decays of the CdS/dendrimer nanoparticles

| Exc. (nm) | n[a] | τ (ns) | $\alpha_i$ | $f_i$ | $X^2_R$ |
|---|---|---|---|---|---|
| 395 | 1 | 61.8 | 1.0 | 1.0 | 1,136.9 |
|  | 2 | 6.2 | 0.747 | 0.137 |  |
|  |  | 116.0 | 0.253 | 0.863 | 32.0 |
|  | 3 | 3.1 | 0.748 | 0.090 |  |
|  |  | 50.2 | 0.163 | 0.319 |  |
|  |  | 169.8 | 0.089 | 0.591 | 1.1 |
| 325 | 1 | 52.3 | 1.0 | 1.0 | 991.5 |
|  | 2 | 7.8 | 0.705 | 0.160 |  |
|  |  | 97.9 | 0.295 | 0.890 | 37.5 |

TABLE I-continued

Frequency-domain intensity and anisotropy decays of the CdS/dendrimer nanoparticles

| Exc. (nm) | $n^a$ | $\tau$ (ns) | $\alpha_i$ | $f_i$ | $X^2_R$ |
|---|---|---|---|---|---|
| | 3 | 2.7 | 0.699 | 0.080 | |
| | | 39.5 | 0.205 | 0.341 | |
| | | 142.8 | 0.096 | 0.579 | 1.7 |

[a]Number of exponents

At an excitation of 395 nm and an $n^a$ of 1, the following anisotropy decay values are seen: $\theta_k$=2,430.5 ns; $r_{0k}$=0.228; and $X^2_R$=0.6

TABLE II

Frequency-domain intensity decay of the $Cd^{2+}$ enriched nanoparticles

| Exc. (nm) | $n^a$ | $\tau$ (ns) | $\alpha_i$ | $f_i$ | $X^2_R$ |
|---|---|---|---|---|---|
| 442 | 1 | 597.50 | 1.00 | 1.00 | 1,656 |
| | 2 | 290.40 | 0.932 | 0.448 | |
| | | 4,907 | 0.068 | 0.552 | 242.90 |
| | 3 | 150.00 | 0.749 | 0.188 | |
| | | 1,171 | 0.243 | 0.476 | |
| | | 25,320 | 0.008 | 0.336 | 2.70 |
| 325 | 1 | 680.20 | 1.00 | 1.00 | 1212.30 |
| | 2 | 425.00 | 0.932 | 0.474 | |
| | | 6,471 | 0.068 | 0.526 | 93.50 |
| | 3 | 241.60 | 0.717 | 0.227 | |
| | | 1,173 | 0.273 | 0.421 | |
| | | 27,783 | 0.010 | 0.352 | 2.90 |

[a]Number of exponents

TABLE III

Intensity decay of the nanoparticles with and without quenchers.

| Compound/Conditions | $\tau$(avgas) (ns) | $\alpha_1$ | $\tau_1$ (ns) | $\alpha_2$ | $\tau_2$ (ns) | $\alpha_3$ | $\tau_3$ (ns) | $X^2_R$ |
|---|---|---|---|---|---|---|---|---|
| blue, no quencher | 106.0 | 0.698 | 4.91 | 0.256 | 57.7 | 0.046 | 214.2 | 2.2 |
| blue + 0.2 M acrylamide | 73.7 | 0.737 | 1.07 | 0.190 | 18.0 | 0.073 | 105.9 | 4.2 |
| blue + 0.2 M iodide | 36.7 | 0.786 | 1.11 | 0.175 | 11.2 | 0.039 | 67.3 | 4.6 |
| red, no quencher | 9.80 | 0.652 | 232.5 | 0.337 | 1073.3 | 0.011 | 2580 | 3.8 |
| red + 0.2 M acrylamide | 8.54 | 0.761 | 229.3 | 0.229 | 1173.0 | 0.010 | 2349 | 1.9 |
| red + 0.2 M iodide | 4.09 | 0.738 | 56.3 | 0.243 | 673.7 | 0.019 | 858.2 | 3.2 |

[b]The excitation was 325 nm. The emission filter for the blue particles was an interference filter 500 +/- 20 nm. The emission filter for the red particles was a long pass filter at 580 nm.

[c]$\tau(avgas) = \sum_i f_i \tau(avgas)i$;

$f_i = \alpha_i \tau_i / \left( \sum_j \alpha_j \tau_j \right)$

We claim:

1. A fluorescent nanoparticle comprising
   cadmium sulfide; and
   at least one dendrimer.

2. A fluorescent nanoparticle of claim 1 wherein said at least one dendrimer is selected from the group consisting of amine-terminated dendrimer, poly(amidoamine) dendrimer, poly(amidoamino-organosilicon) dendrimer having hydrophilic domains and hydrophobic domains, star polymers, self-assemblying polymers, and zeolites.

3. A fluorescent powder comprising:
   a plurality of the fluorescent nanoparticles of claim 1 wherein said fluorescent nanoparticles have an average critical dimension ranging from approximately 2 nm to approximately 5 nm and wherein the majority of the plurality of said fluorescent nanoparticles have a size distribution within approximately +/-15% of the average critical dimension.

4. A fluorescent power of claim 3 wherein said at least one dendrimer is selected from the group comprising amine-terminated dendrimer, poly(amidoamine) dendrimer, poly(amidoamino-organosilicon) dendrimer having hydrophilic domains and hydrophobic domains, star polymers, self-assemblying polymers, and zeolites.

5. A process for making the fluorescent nanoparticle of claim 1 comprising
   mixing a $Cd(NO_3)_2 \cdot 4H_2O$ methanol solution with a molar equivalent methanol solution of dendrimer; and
   adding $Na_2S$ while in deoxygenated environment.

6. The fluorescent nanoparticle of claim 1, wherein the fluorescent nanoparticle has a wavelength emission of at least 500 nm and a decay lifetime of at least 30 ns.

7. A sensor for the measuring of the concentration of an analyte or the absence of an analyte in a sample, said sensor comprising:
   a signal emitting probe further comprising a fluorescent nanoparticle of claim 1;
   a light source;
   a light filter;
   a fluorescent light detector;
   a fluorescence measurement system; and
   a data analysis system wherein said data analysis system converts the measured fluorescence of a signal to a concentration for an analyte.

8. A fluorescent nanoparticle comprising
   cadmium sulfide; and
   polyphosphate.

9. A fluorescent powder comprising:
   a plurality of the fluorescent nanoparticles of claim 8 wherein said fluorescent nanoparticles have an average critical dimension ranging from approximately 2 nm to approximately 5 nm and wherein the majority of the plurality of said fluorescent nanoparticles have a size distribution within approximately +/-15% of the average critical dimension.

10. A process for making a fluorescent nanoparticle of claim 8 comprising:

mixing a $Cd(NO_3)_2 \cdot 4H_2O$ methanol solution with a molar equivalent methanol solution of $Na_6(PO_3)_6$; and adding $Na_2S$ while in deoxygenated environment.

11. The fluorescent nanoparticle of claim 8, wherein the fluorescent nanoparticle has a wavelength emission of at least 500 nm and a decay lifetime of at least 30 ns.

12. A sensor for the measuring of the concentration of an analyte or the absence of an analyte in a sample, said sensor comprising:

a signal emitting probe further comprising a fluorescent nanoparticle of claim 8;

a light source;

a light filter;

a fluorescent light detector;

a fluorescence measurement system; and a data analysis system wherein said data analysis system converts the measured fluorescence of a signal to a concentration for an analyte.

* * * * *